(12) United States Patent
Klotz

(10) Patent No.: US 8,002,838 B2
(45) Date of Patent: Aug. 23, 2011

(54) JOINT PROSTHESIS WITH POSITIONABLE HEAD

(75) Inventor: Conrad L. Klotz, Nappanee, IN (US)

(73) Assignee: DePuy Products, Inc., Warsaw, IN (US)

(*) Notice: Subject to any disclaimer, the term of this patent is extended or adjusted under 35 U.S.C. 154(b) by 253 days.

(21) Appl. No.: 12/137,378

(22) Filed: Jun. 11, 2008

(65) Prior Publication Data

US 2009/0312838 A1   Dec. 17, 2009

(51) Int. Cl.
  A61F 2/40   (2006.01)
  A61F 2/32   (2006.01)
(52) U.S. Cl. .................. 623/19.14; 623/22.45
(58) Field of Classification Search ............... 623/22.45, 623/23.18, 23.35, 23.45, 19.11, 19.12, 19.14
See application file for complete search history.

(56) References Cited

U.S. PATENT DOCUMENTS

| | | | |
|---|---|---|---|
| 4,003,095 A | 1/1977 | Gristina | |
| 4,822,370 A | 4/1989 | Schelhas | |
| 5,076,541 A | 12/1991 | Daghe et al. | |
| 5,080,685 A | 1/1992 | Bolesky et al. | |
| 5,314,479 A | 5/1994 | Rockwood, Jr. et al. | |
| 5,358,526 A | 10/1994 | Tornier | |
| 5,370,706 A | 12/1994 | Bolesky et al. | |
| 5,702,457 A | 12/1997 | Walch et al. | |
| 5,725,597 A | 3/1998 | Hwang | |
| 5,741,335 A | 4/1998 | Gerber et al. | |
| 5,743,898 A | 4/1998 | Bailey et al. | |
| 5,910,143 A | 6/1999 | Cripe et al. | |
| 6,197,062 B1 | 3/2001 | Fenlin | |
| 6,203,575 B1 | 3/2001 | Farey | |
| 6,206,925 B1 | 3/2001 | Tornier | |
| 6,228,120 B1 | 5/2001 | Leonard et al. | |
| 6,283,999 B1 | 9/2001 | Rockwood, Jr. | |
| 6,328,748 B1 | 12/2001 | Hennig | |
| 6,361,566 B1 | 3/2002 | Al-Hafez | |
| 6,478,500 B1 | 11/2002 | Farenholtz | |
| 6,558,425 B2 | 5/2003 | Rockwood, Jr. | |

(Continued)

FOREIGN PATENT DOCUMENTS

DE    4445892    6/1996

(Continued)

OTHER PUBLICATIONS

European Search Report in corresponding application (09162325.6-1526), mailed Oct. 2, 2009, 6 pages.

(Continued)

*Primary Examiner* — Bruce E Snow (74) *Attorney, Agent, or Firm* — Maginot, Moore & Beck (57) ABSTRACT

A prosthesis assembly in one embodiment includes a stem configured to be implanted in a bone and including a first coupling portion, a head having a bearing surface configured to mate with at least one of a natural opposing joint component and a prosthetic opposing joint component, the head further having a second coupling portion, a coupler including a third coupling portion and a fourth coupling portion, the third coupling portion configured to couple with the second coupling portion, and an insert including (i) a fifth coupling portion configured to couple with the fourth coupling portion in any of a plurality of rotational orientations in combination with any of a plurality of roll angles and any of a plurality of pitch angles, and (ii) a sixth coupling portion configured to couple with the first coupling portion only when the insert assumes a predetermined rotational orientation with respect to the stem.

5 Claims, 10 Drawing Sheets

U.S. PATENT DOCUMENTS

| | | |
|---|---|---|
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,736,851 B2 | 5/2004 | Maroney et al. |
| 6,736,852 B2 | 5/2004 | Callaway et al. |
| 6,749,637 B1 | 6/2004 | Bahler |
| 6,776,799 B2 | 8/2004 | Ball et al. |
| 6,953,478 B2 | 10/2005 | Bouttens et al. |
| 7,192,449 B1 | 3/2007 | McQueen et al. |
| 2001/0041940 A1 | 11/2001 | Pearl |
| 2001/0053935 A1 | 12/2001 | Hartdegen et al. |
| 2002/0016634 A1 | 2/2002 | Maroney et al. |
| 2003/0014112 A1 | 1/2003 | Ralph et al. |
| 2003/0040802 A1 | 2/2003 | Errico et al. |
| 2003/0097183 A1 | 5/2003 | Rauscher et al. |
| 2004/0002765 A1 | 1/2004 | Maroney et al. |
| 2004/0010261 A1 | 1/2004 | Hoag et al. |
| 2004/0030400 A1 | 2/2004 | Horber |
| 2004/0064142 A1 | 4/2004 | Ball et al. |
| 2004/0064188 A1 | 4/2004 | Ball et al. |
| 2004/0064189 A1 | 4/2004 | Maroney et al. |
| 2004/0122440 A1 | 6/2004 | Daniels et al. |
| 2004/0167629 A1 | 8/2004 | Geremakis et al. |
| 2005/0113931 A1 | 5/2005 | Horber |
| 2005/0143829 A1 | 6/2005 | Ondrla et al. |
| 2005/0187637 A1 | 8/2005 | Karrer et al. |
| 2005/0251263 A1 | 11/2005 | Forrer et al. |
| 2005/0288681 A1 | 12/2005 | Klotz et al. |
| 2006/0142872 A1 | 6/2006 | Klotz et al. |
| 2007/0078519 A1 | 4/2007 | Klotz |

FOREIGN PATENT DOCUMENTS

| | | |
|---|---|---|
| DE | 19509037 | 9/1996 |
| DE | 19509037 C1 | 9/1996 |
| DE | 19951141 | 5/2001 |
| DE | 10123517 | 11/2002 |
| DE | 202005020876 | 10/2006 |
| EP | 0549480 | 6/1993 |
| EP | 0679375 | 11/1995 |
| EP | 0712617 A1 | 5/1996 |
| EP | 0715836 A1 | 6/1996 |
| EP | 0931522 A1 | 7/1999 |
| EP | 1186278 | 3/2002 |
| EP | 1314407 A1 | 5/2003 |
| EP | 1321114 A1 | 6/2003 |
| EP | 1393697 | 3/2004 |
| EP | 1402856 A1 | 3/2004 |
| EP | 1681037 | 7/2006 |
| EP | 1769776 | 4/2007 |
| FR | 2731612 A1 | 9/1996 |
| JP | 2004512922 | 5/2003 |
| WO | 9303688 | 3/1993 |
| WO | 1993003688 A1 | 3/1993 |
| WO | 0122905 | 4/2001 |
| WO | 0239932 | 5/2002 |
| WO | 03096870 | 11/2003 |
| WO | 03096939 | 11/2003 |

OTHER PUBLICATIONS

The McElroy Translation Company, English translation of German patent No. DE 101 23 517 C1, Jan. 2006 (20 pages).

Japan Patent Office, Notification of Reasons for Refusal (Translation) associated with patent application 2006-267228, 4 pages, mailing date Oct. 5, 2010.

JOINT PROSTHESIS WITH POSITIONABLE HEAD

FIELD

The present disclosure relates to joint prostheses, and particularly to prostheses having articulating head components. More specifically, the disclosure relates to a system for achieving variable positions for the head component of a joint prosthesis relative to a bone-engaging portion of the prosthesis.

BACKGROUND

Repair and replacement of human joints, such as the knee, shoulder, elbow and hip, has become a more and more frequent medical treatment. Longer life spans mean that the joints are subjected to wear and tear over an extended period of time. Additionally, participation in sports activities results in a greater likelihood of serious joint injuries. Treatment of injuries, wear, and disease in human joints has progressed from the use of orthotics to mask the problem, to fusion of the joint, to the use of prostheses to replace the damaged joint component(s).

As the success rate for total or partial joint replacements has increased, so too has the need for modularity and universality in the joint prosthesis. Patient variety means that no single size or configuration of joint prosthesis provides optimum results for each patient. The physical dimensions of a patient's joint components vary, as do the bio-mechanic relationship between the components within a particular joint. By way of example, in a shoulder prosthesis, the relationship between the articulating humeral and glenoid components can be significantly different between patients. These relationships are especially important where only one component of the joint is being replaced and must integrate with the existing natural opposing joint component.

For instance, in many shoulder surgeries, only the humeral component is replaced, leaving the glenoid component intact. In this case, it is imperative that the articulating surface of the humeral component match the articulating surface of the glenoid component as perfectly as possible, both statically and dynamically. With a typical humeral prosthesis, version and inclination are adjusted by the geometry of the head of the prosthesis. In other words, certain pre-determined head geometries are available that can be selected for a mating glenoid component. Unless a virtually infinite variety of pre-determined head geometries are maintained in inventory, the resulting humeral prosthesis will rarely provide an optimum fit with the glenoid component of the shoulder joint.

In a typical surgical procedure, a trial component is used to determine the optimum component configuration for the permanent prosthetic device. In most cases, the surgeon is able to make a selection of components and configurations that fits the joint in an acceptable manner. In some cases, however, the functionality of the fit cannot be fully assessed until the surgery is completed and the patient has had an opportunity to utilize the repaired joint. In some cases, a revision surgery is necessary to replace a prosthetic device that is not optimally sized or configured for the particular patient. One type of revision surgery requires removal of the entire prosthesis from the bone and replacement with a different prosthesis.

There is a significant need for a joint prosthesis that is both modular and universal. A further need exists for a prosthesis that is easily manipulated during the surgery and capable being configured in a nearly infinite number of version and inclination angle combinations. Additionally, a need exists for a prosthetic device that is easily modified during a revision surgery. Yet a further need exists for a prosthetic device that is modifiable during a revision surgery without the need to completely remove the entire prosthetic assembly from the bone of the patient.

SUMMARY

A method and assembly for achieving variable positions of a head component of a joint prosthesis relative to a bone-engaging portion of the prosthesis is disclosed. In a one embodiment, a prosthesis assembly includes a stem configured to be implanted in a bone and including a first coupling portion, a head having a bearing surface configured to mate with at least one of a natural opposing joint component and a prosthetic opposing joint component, the head further having a second coupling portion, a coupler including a third coupling portion and a fourth coupling portion, the third coupling portion configured to couple with the second coupling portion, and an insert including (i) a fifth coupling portion configured to couple with the fourth coupling portion in any of a plurality of rotational orientations in combination with any of a plurality of roll angles and any of a plurality of pitch angles, and (ii) a sixth coupling portion configured to couple with the first coupling portion only when the insert assumes a predetermined rotational orientation with respect to the stem.

In a further embodiment, a prosthesis assembly kit includes at least one stem configured to be implanted in a bone, the at least one stem including a keyed stem coupling portion, a plurality of heads, each of the plurality of heads having a bearing surface configured to mate with at least one of a natural opposing joint component and a prosthetic opposing joint component, each of the plurality of heads further having a head coupling portion, at least one first coupler including an upper coupling portion and a lower coupling portion, the upper coupling portion configured to couple with the head coupling portion of each of the plurality of heads, and at least one insert including (i) a non-keyed insert coupling portion configured to couple with the lower coupling portion of each of the at least one first couplers in any of a plurality of rotational orientations in combination with any of a plurality of roll angles and any of a plurality of pitch angles, and (ii) a keyed insert coupling portion configured to couple with the keyed stem coupling portion of each of the at least one stems.

In yet another embodiment, a method of forming a prosthesis includes implanting a stem in a bone, the stem including a first coupling portion, determining a desired orientation of a head with respect to the stem, coupling the head with a first coupling portion of a coupler, coupling a second coupling portion of the coupler with an insert, aligning a key member of the coupled insert with the implanted stem, and coupling the aligned insert with the implanted stem.

The above-noted features and advantages, as well as additional features and advantages, will be readily apparent to those skilled in the art upon reference to the following detailed description and the accompanying drawings.

BRIEF DESCRIPTION OF THE DRAWINGS

The illustrative devices will be described hereinafter with reference to the attached drawings which are given as non-limiting examples only, in which.

Corresponding reference characters indicate corresponding parts throughout the several views.

DETAILED DESCRIPTION

For the purpose of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
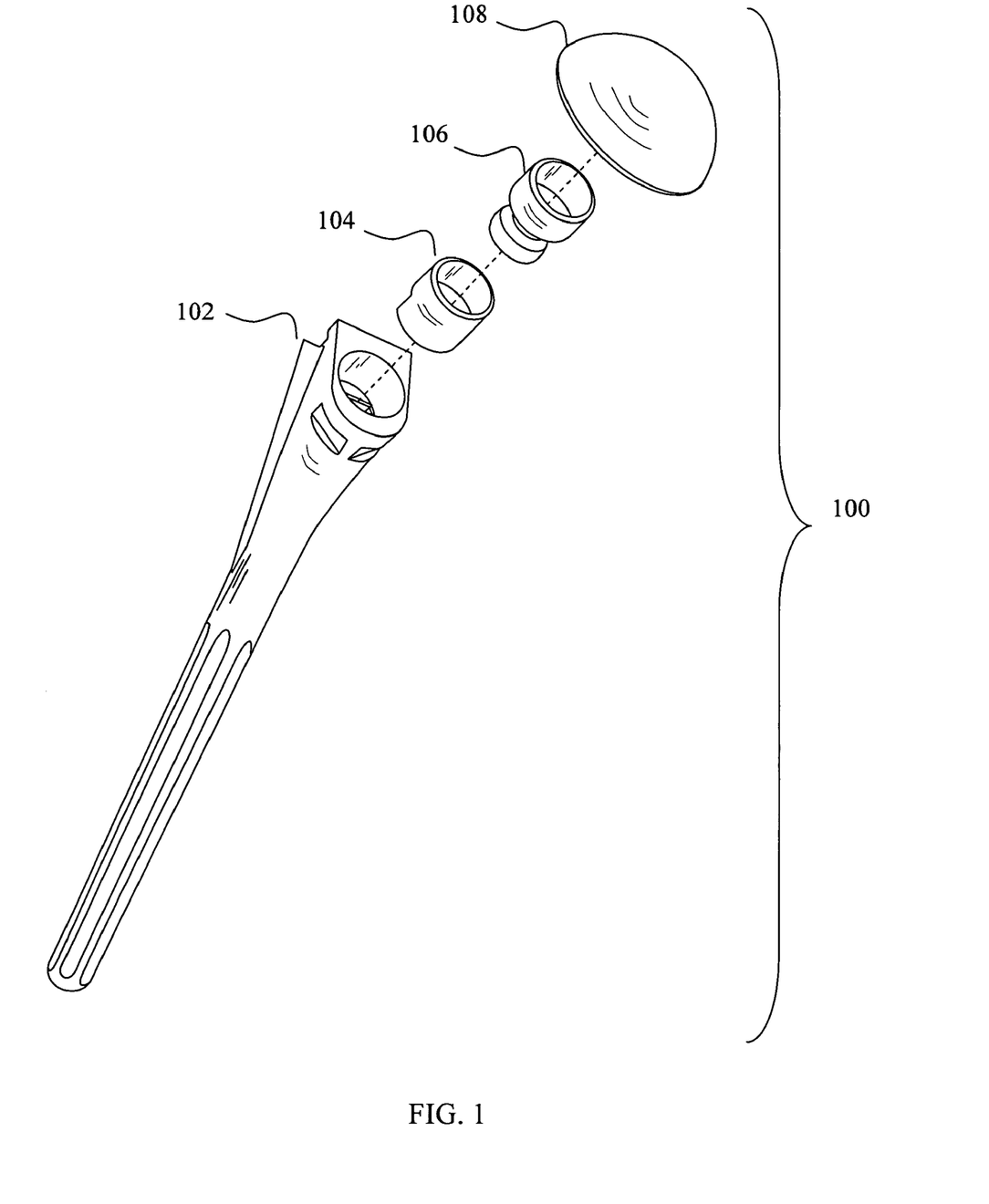
FIG. 1 depicts a perspective exploded view of a prosthesis assembly including a stem, an insert, a coupler and a head incorporating principles of the invention.

FIG. 1 depicts a perspective view of a humeral prosthesis assembly 100. The assembly 100 is the humeral component of a shoulder prosthesis that can be implanted in the humerus bone of a patient for articulating engagement with the natural glenoid or with a glenoid prosthesis. The assembly 100 includes a stem 102 configured to be implanted within the humerus bone in an acceptable manner. The assembly 100 further includes an insert 104, a coupler 106 and an articulating head component 108.

Figures 2, 3, 4:
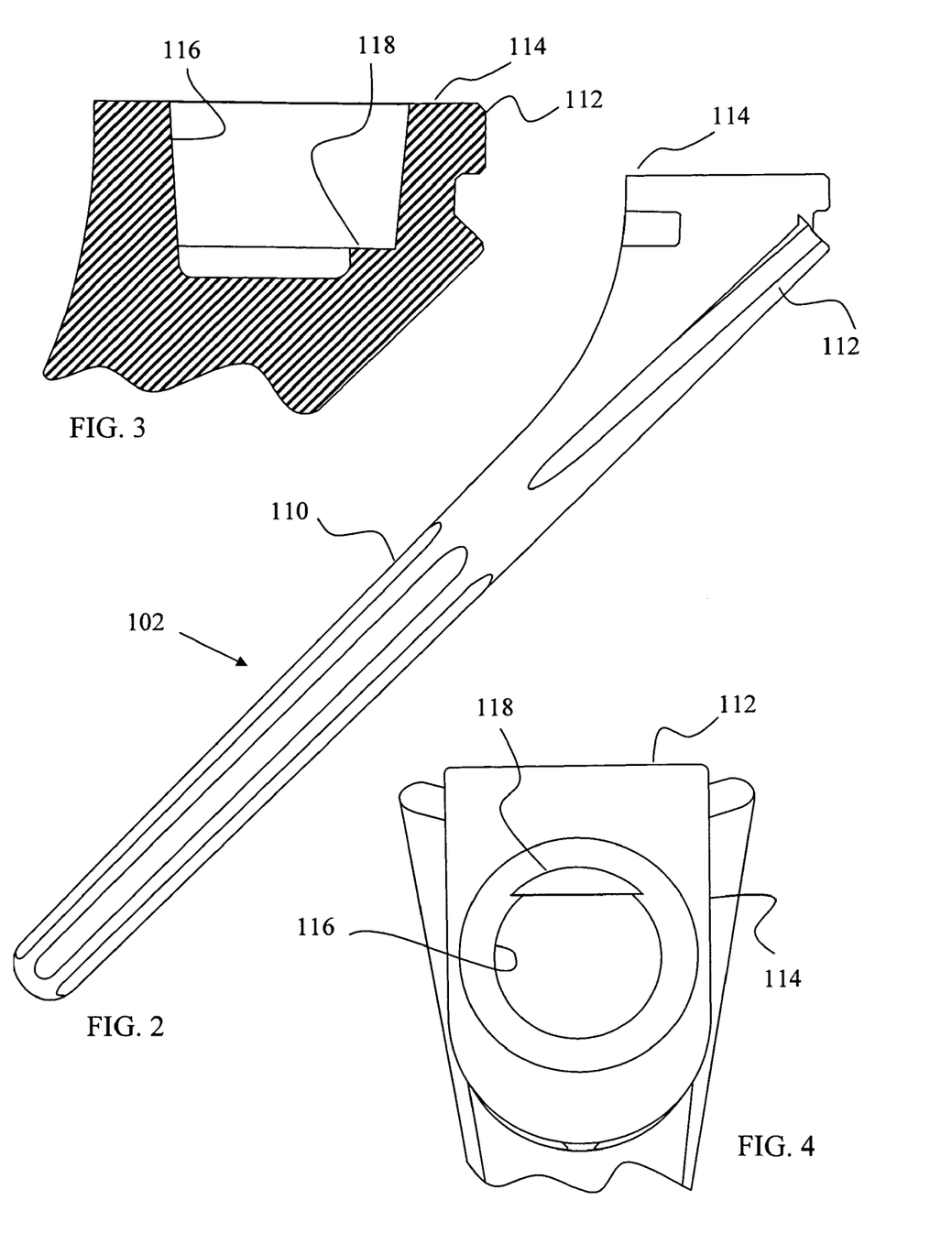
FIG. 2 depicts a side plan view of the stem of FIG. 1.
FIG. 3 depicts a partial cross sectional view of the stem of FIG. 1 showing a coupling receptacle with a key feature.
FIG. 4 depicts a partial top plan view of the stem of FIG. 1 showing the coupling receptacle with the key feature.

With further reference to FIGS. 2-4, the stem 102 includes a shaft 110 and a platform area 112. The platform area 112 includes an upper surface 114 that faces toward the glenoid component of the joint when the stem 102 is implanted within a patient. The upper surface 114 defines a tapered bore 116 that includes a key member 118.

Figure 5:
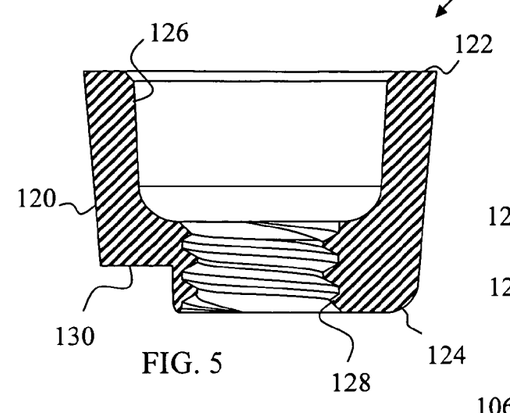
FIG. 5 depicts a cross sectional view of the insert of FIG. 1 showing an inner coupling receptacle and an outer coupling wall with a key feature.
Figure 6:
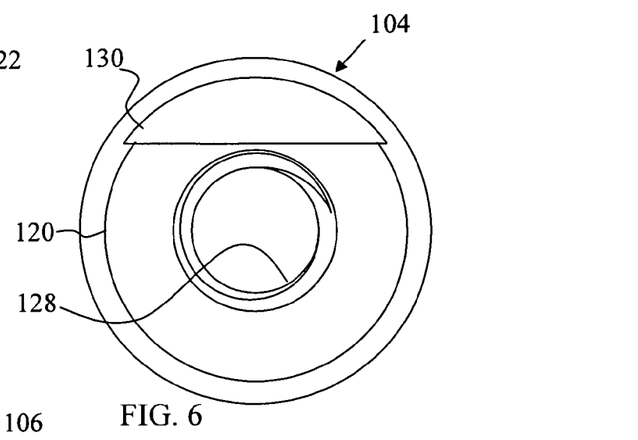
FIG. 6 depicts a bottom plan view of the insert of FIG. 5 showing the periphery of the outer coupling wall and the key feature.

The insert 104, shown in FIGS. 1, 5, and 6, includes an outer wall 120 which generally tapers from an upper portion 122 to a lower portion 124. A tapered bore 126 opens to the upper portion 122 and a threaded bore 128 opens at one end to the lower portion 124 and opens at the other end to the tapered bore 126. A key member 130 is located near the lower portion 124.

Figure 7:
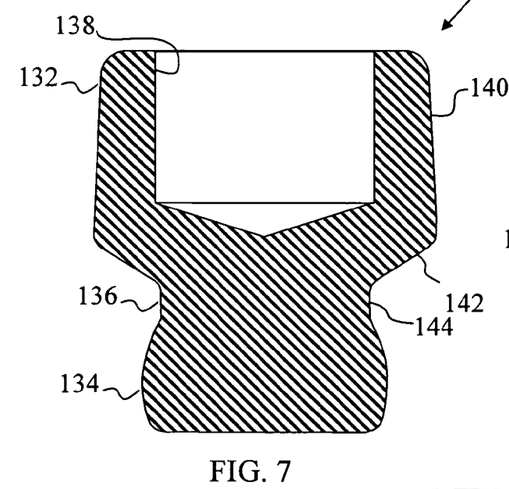
FIG. 7 depicts a cross sectional view of the coupler of FIG. 1 showing an upper coupling wall and an lower bulbous coupling.
Figure 8:
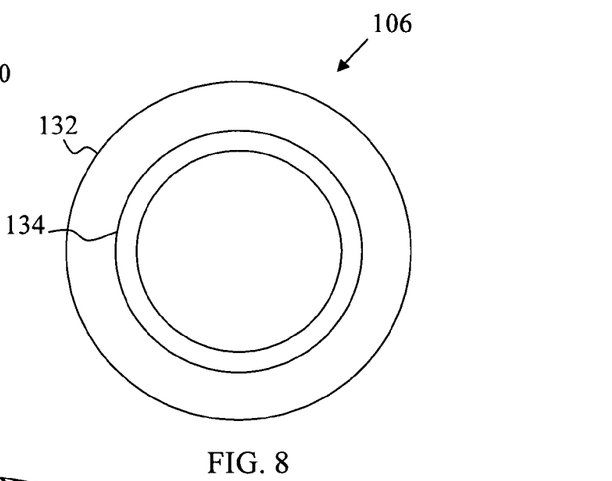
FIG. 8 depicts a bottom plan view of the coupler of FIG. 7 showing the bulbous coupling to be circular in plan view.

The coupler 106 includes an upper coupling portion 132 and a lower coupling portion 134 joined by a middle portion 136 as shown in FIGS. 7 and 8. The upper coupling portion 132 includes a bore 138 and a tapered outer wall 140. The middle portion 136 includes a shoulder portion 142 which tapers inwardly from the tapered outer wall 140 to a neck portion 144. The lower coupling portion 134 is bulbous shaped when viewed in profile (FIG. 7) and circular when viewed in plan (see FIG. 8).

Figure 9:
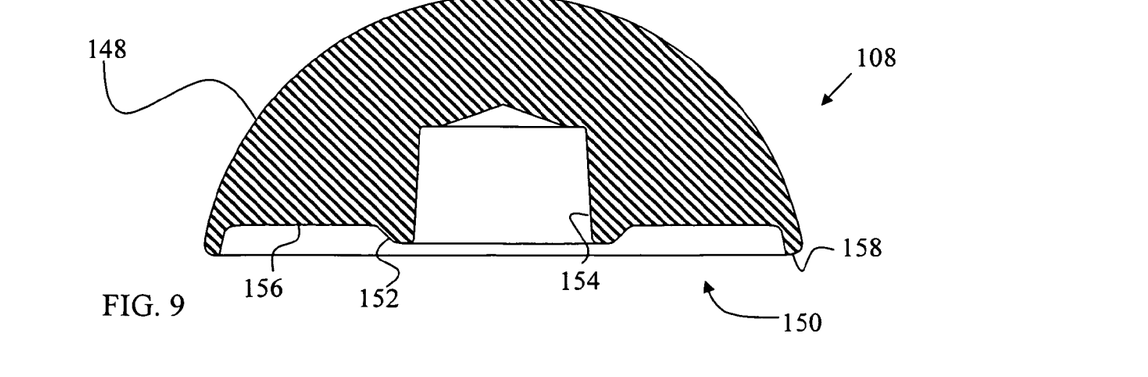
FIG. 9 depicts a cross sectional view of the head of FIG. 1 showing an upper articulating surface and a lower surface including a coupling receptacle and a recessed area.

Referring to FIGS. 1 and 9, the articulating head component 108 includes an outer articulating surface 148, which is shaped to articulate with a glenoid component, and a lower surface 150. The lower surface 150 includes a protuberance 152 defining a tapered bore 154. A recessed area 156 extends between the protuberance 152 and a lip 158 which circumscribes the lower surface 150.

Figure 10:
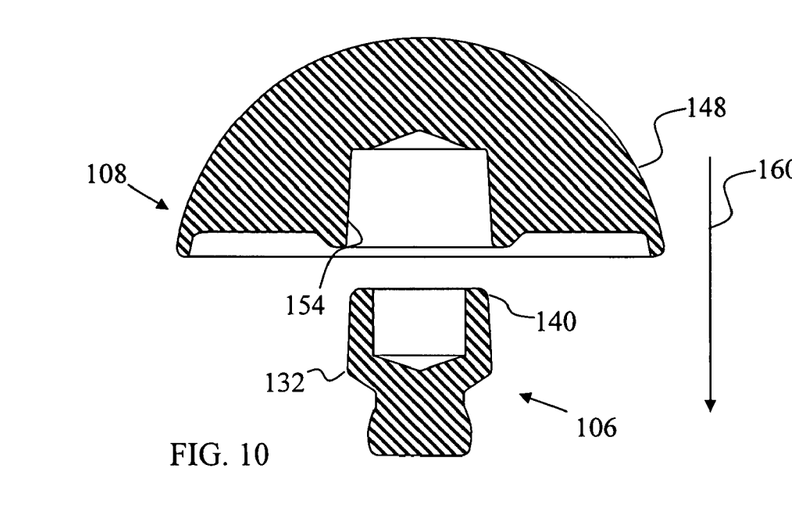
FIGS. 10-13 depict a procedure of coupling of the head of FIG. 1 with the coupler of FIG. 1 and coupling the coupler of FIG. 1 with the insert of FIG. 1 which may be accomplished prior to implantation in accordance with principles of the invention.

Assembly of the humeral prosthesis assembly 100 in one embodiment may be performed once the stem 102 has been implanted within the bone of a patient. A trial (not shown) is used to determine the head size and the version and inclination angle combination of the head that provides the desired joint configuration. The coupler 106 may then be joined with the articulating head component 108 of the desired size by aligning the tapered bore 154 with the upper coupling portion 132 as shown in FIG. 10.

Figure 11:
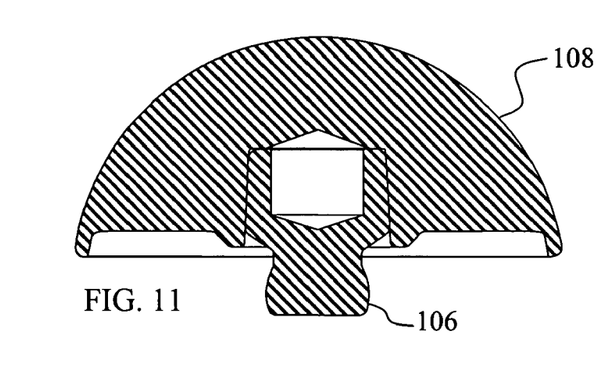

The tapered bore 154 and the outer wall 140 of the upper coupling portion 132 in this embodiment have a five degree taper. The tapered bore 154 and the outer wall 140 thus provide for a Morse taper coupling. Accordingly, movement of the articulating head component 108 in the direction of the arrow 160 onto the upper coupling portion 132 provides the configuration of FIG. 11. The articulating head component 108 and the coupler 106 are then firmly coupled by impacting the articulating head component 108 onto the coupler 106.

Figure 12:
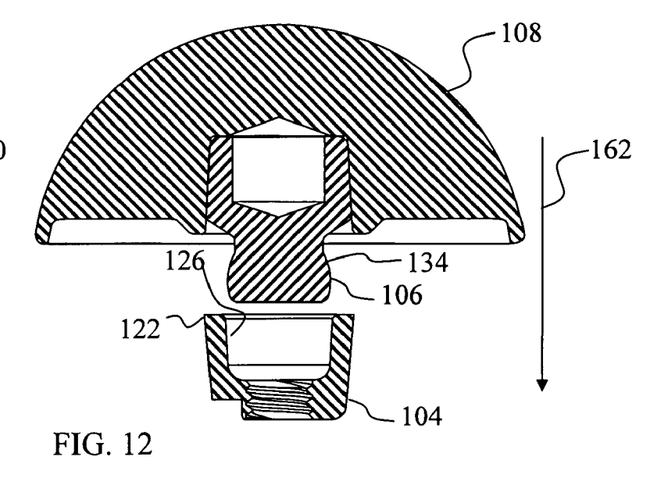
Figure 13:
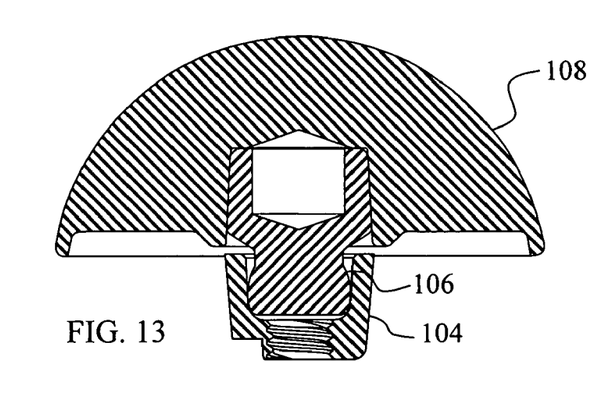

With reference to FIG. 12, the lower coupling portion 134 of the coupler 106 is then aligned with the tapered bore 126 of the insert 104 and the articulating head component 108 and the coupler 106 are moved in the direction of the arrow 162. Insertion and impacting of the lower coupling portion 134 within the tapered bore 126 results in the configuration of FIG. 13. Specifically, the lower coupling portion 134 has a diameter that is larger than the diameter of the tapered bore 126 at a location spaced apart from the upper portion 122 of the insert 104. Thus, while a Morse taper coupling is not formed, the lower coupling portion 134 may be firmly secured within the tapered bore 126 by application of sufficient force. Preferably, the force used to secure the lower coupling portion 134 within the tapered bore 126 is greater than the force used when forming a Morse taper coupling.

Figure 14:
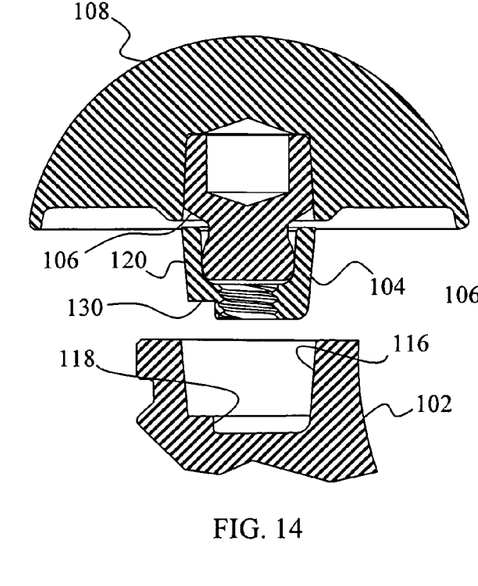
FIGS. 14-15 depict a procedure of alignment the key member of the insert of FIG. 1 with the key member of the stem of FIG. 1 and coupling of the insert with the stem.

Once the head 108, the coupler 106 and the insert 104 have been coupled, the lower portion 124 of the insert 104 is aligned with the tapered bore 116 as shown in FIG. 14. The key member 130 and the key member 118 are configured such that the lower portion 124 may be fully inserted into the tapered bore 116 in a single rotational configuration. Accordingly, the insert 104 must be rotated as necessary to align the key member 130 and the key member 118. Consequently, the axis of the bore 116 is collocated with the axis of the insert 104.

The tapered bore 116 and the outer wall 120 of the insert 104 in this embodiment have a ten degree taper. The tapered bore 116 and the outer wall 120 thus provide for a Morse taper coupling. Accordingly, movement of the insert 104 in the direction of the arrow 164 into the tapered bore 116 provides the configuration of FIG. 15. The insert 104 and the stem 102 are then firmly coupled by impacting the articulating head component 108 to force the articulating head component 108, the coupler 106 and the insert 104 toward the stem 102.

Alternatively, the coupler 106 and the insert 104 may be positioned with the implanted stem 102 prior to coupling the head 108 with the coupler 106. The head 108 is then positioned and coupled with the previously positioned coupler 106 and the insert 104. This alternative may be used in rescission surgeries to allow for a smaller incision to be used to access the surgical site.

Figure 15:
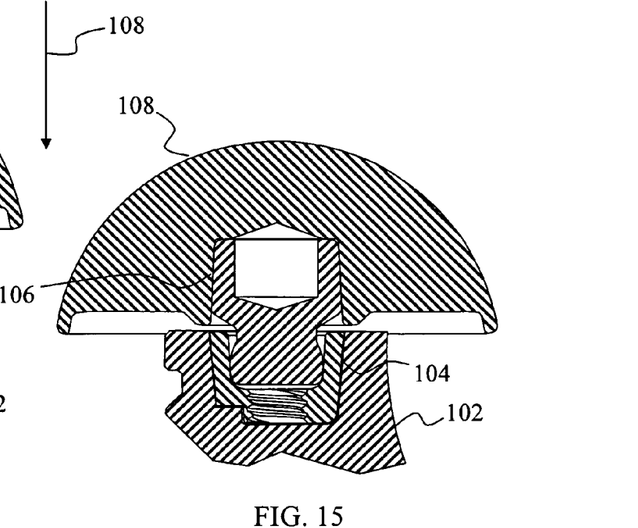

FIG. 15 depicts a configuration wherein the axes of the tapered bore 154 of the articulating head component 108, the coupler 106, the insert 104 and the tapered bore 116 are substantially aligned. Because the articulating head component 108 and the coupler 106 form a Morse taper coupling as discussed above, the articulating head component 108 will assume a specific axial alignment with respect to the coupler 106 when the articulating head component 108 is coupled with the coupler 106. Likewise, because the insert 104 and the stem 102 form a Morse taper coupling as discussed above, the insert 104 will assume a specific axial alignment with respect to the stem 102 when the insert 104 is coupled with the stem 102.

Therefore, the axial alignment of the articulating head component 108 with respect to the stem 102 may be established by controlling the axial alignment of the coupler 106 with the insert 104. Moreover, the key members 118 and 130 establish a specific rotational alignment of the insert 104 with respect to the stem 102. Therefore, the rotational orientation of the articulating head component 108 with respect to the stem 102 may be established by controlling the rotational alignment of the coupler 106 with the insert 104. Accordingly, the desired axial and rotational alignment of the articulating head component 108 with respect to the stem 102 may be established by controlling the rotational and axial alignment of the coupler 106 with the insert 104.

Figure 16:
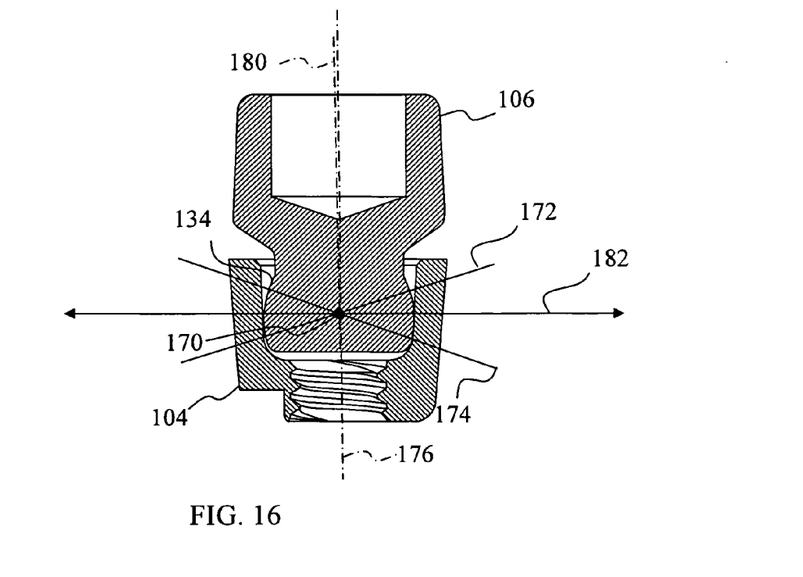
FIGS. 16-19 depict the combinations of version and inclination angles at which the coupler of FIG. 1 may be coupled with the insert of FIG. 1.

Rotational and axial alignment of the coupler 106 with the insert 104 is discussed more fully with initial reference to FIG. 16. FIG. 16 depicts the geometric center 170 of the lower coupling portion 134. The lower coupling portion 134 is formed such that the diameter of the lower coupling portion 134 along a plane that includes the geometric center 170 and is located between the axes 172 and 174 is greater than a diameter of the tapered bore 126 at a location between the upper portion 122 of the insert 104 and the bottom of the tapered bore 126.

Accordingly, the coupler 106 may be coupled with the insert 104 with any axial or rotational alignment so long as the lower coupling portion 134 is oriented within the tapered bore 126 such that a plane that includes the geometric center 170, and is perpendicular to the axis 176 of the insert 104, is located between the axes 172 and 174.

By way of example, the axis 180 of the coupler 106 is aligned with the axis 170 (the axis 180 is depicted as offset from the axis 170 in FIG. 16 for purpose of clarity). Additionally, the plane 182, which includes the geometric center 170, is perpendicular to the axis 176 of the insert 104 and is located between the axes 172 and 174. Accordingly, the coupler 106 and the insert 104 may be coupled in the configuration shown in FIG. 16.

Figure 17:
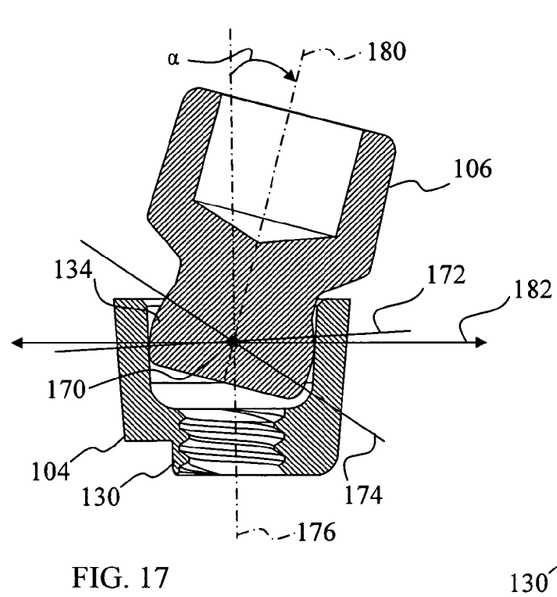
Figure 18:
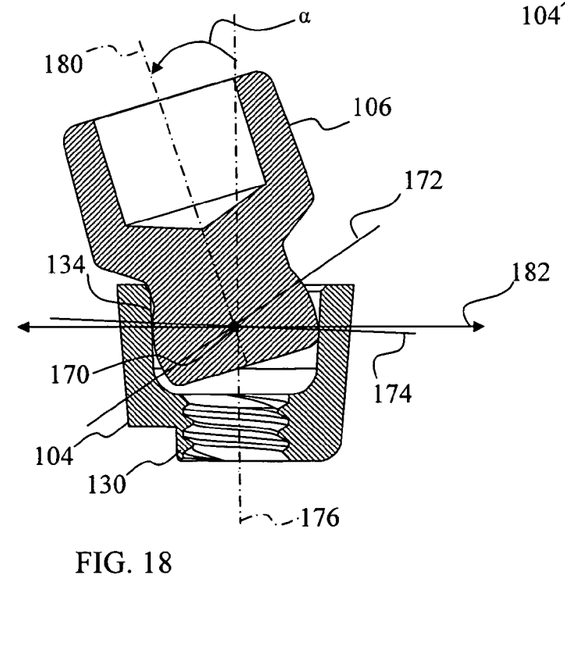

FIG. 17 shows the coupler 106 pivoted in a direction away form the key member 130, thereby generating an angle a between the axis 180 and the axis 170. Nonetheless, the plane 182, which includes the geometric center 170 and is perpendicular to the axis 176 of the insert 104, is still located between the axes 172 and 174. Accordingly, the coupler 106 and the insert 104 may be coupled in the configuration shown in FIG. 17. Similarly, the coupler 106 and the insert 104 may be coupled in the configuration shown in FIG. 18 wherein the coupler 106 is pivoted in a direction toward the key member 130, thereby generating an angle a between the axis 180 and the axis 170.

Figure 19:
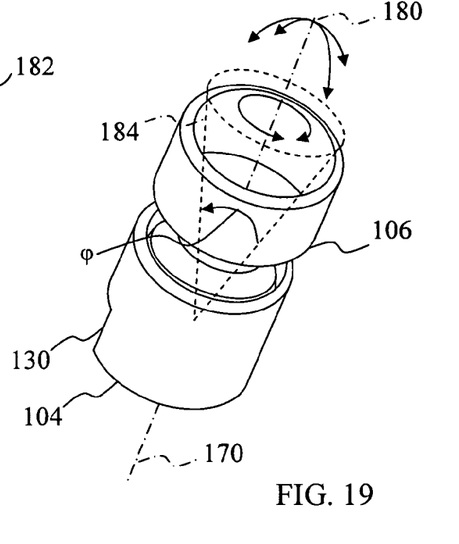

Moreover, because the lower coupling portion 134 is circular when viewed from the bottom (see FIG. 8), the coupler 106 may be pivoted from side to side with respect to the key member 130. Thus, as shown in FIG. 19, the coupler 106 and the insert 104 may coupled in any desired combination of inclination and version angles that positions the axis 180 of the coupler 106 within a cone 184 originating from the axis 170 and having a cone angle of $\phi$. In one embodiment, the coupler 106 may be positioned within about 15 degrees of the axis 180 in any direction, thereby providing a cone angle of about 30 degrees. The cone angle for a particular embodiment is typically limited by impingement of either the insert 104 on the shoulder 142 or impingement of the stem 102 on the lower surface 150. Accordingly, the cone angle may be modified by selection of the shape and dimensions of, for example, the neck 144 and shoulder 142 of the coupler 106, the protuberance 152, the recessed area 156 and the platform 112.

Figures 20, 21, 22:
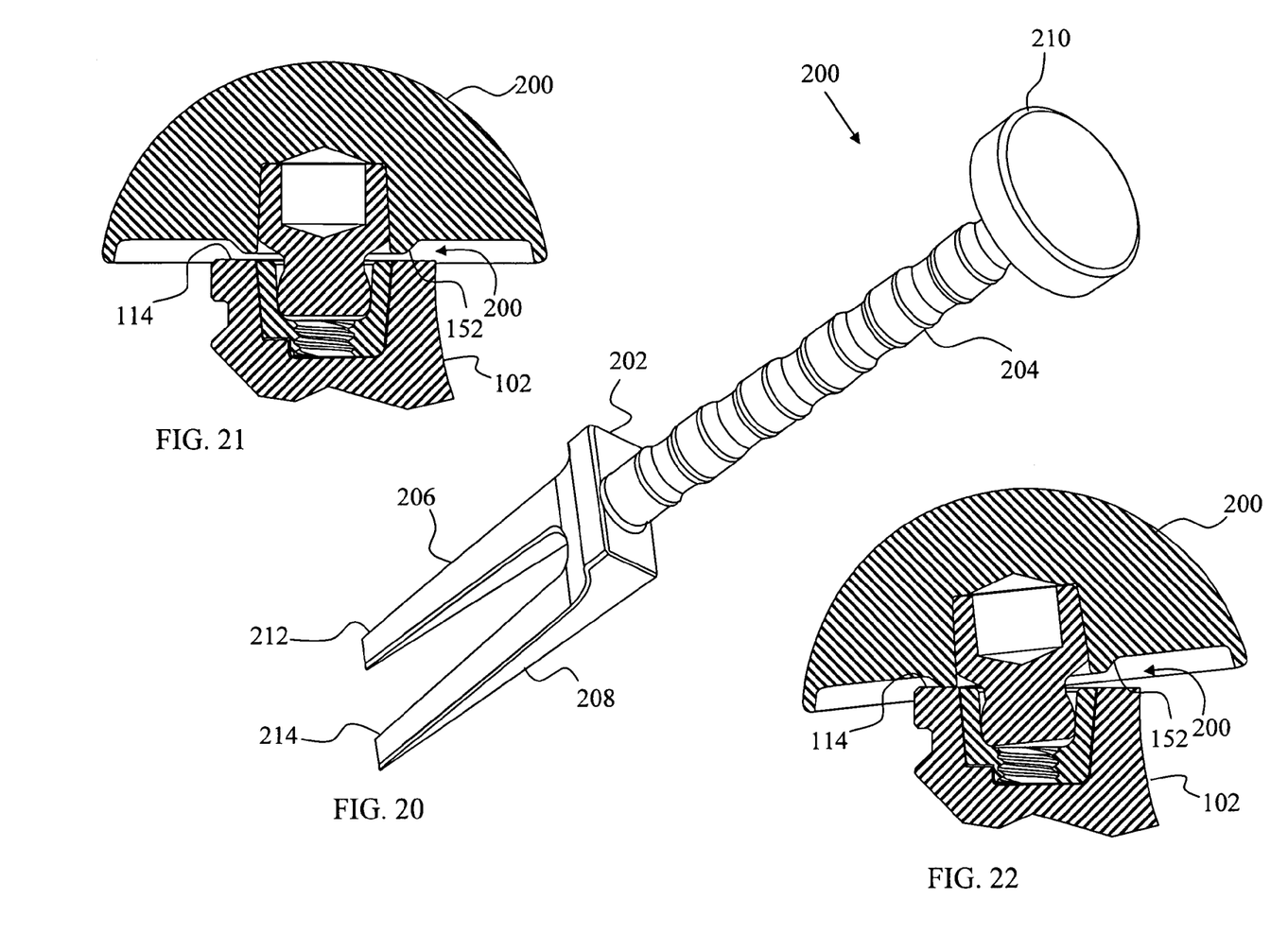
FIG. 20 depicts a perspective view of a removal tool that may be included in a kit and used to decouple the head of FIG. 1 from the coupler of FIG. 1.
FIG. 21 depicts a partial cross sectional view of the assembled prosthesis assembly of FIG. 1 showing a gap into which the prongs of the removal tool of FIG. 20 may be inserted to decouple the head of FIG. 1 from the coupler of FIG. 1.
FIG. 22 depicts a partial cross sectional view of the assembled prosthesis assembly of FIG. 1 showing a gap into which the prongs of the removal tool of FIG. 20 may be inserted to decouple the head of FIG. 1 from the coupler of FIG. 1 when the axis of the head is not aligned with the axis of the stem receptacle.

Disassembly of the assembly 100 is possible using the removal tool 200 of FIG. 20. The removal tool 200 includes a base 202 and a shaft 204. Two prongs 206 and 208 extend outwardly from the base 202 and an impact knob 210 is located on the shaft 204. The prongs 206 and 208 are spaced apart by a distance corresponding to the diameter of the tapered bore 116 and are narrowed at the distal end portions 212 and 214, respectively. The distal end portions 212 and 214 are thus proportioned to fit within a gap 220 (see FIG. 21) between the protuberance 152 and the upper surface 114 of the shaft 102. Even when the articulating head component 108 is angled with respect to the shaft 102 as shown in FIG. 22, the gap 220 is present.

Figures 23, 24, 25:
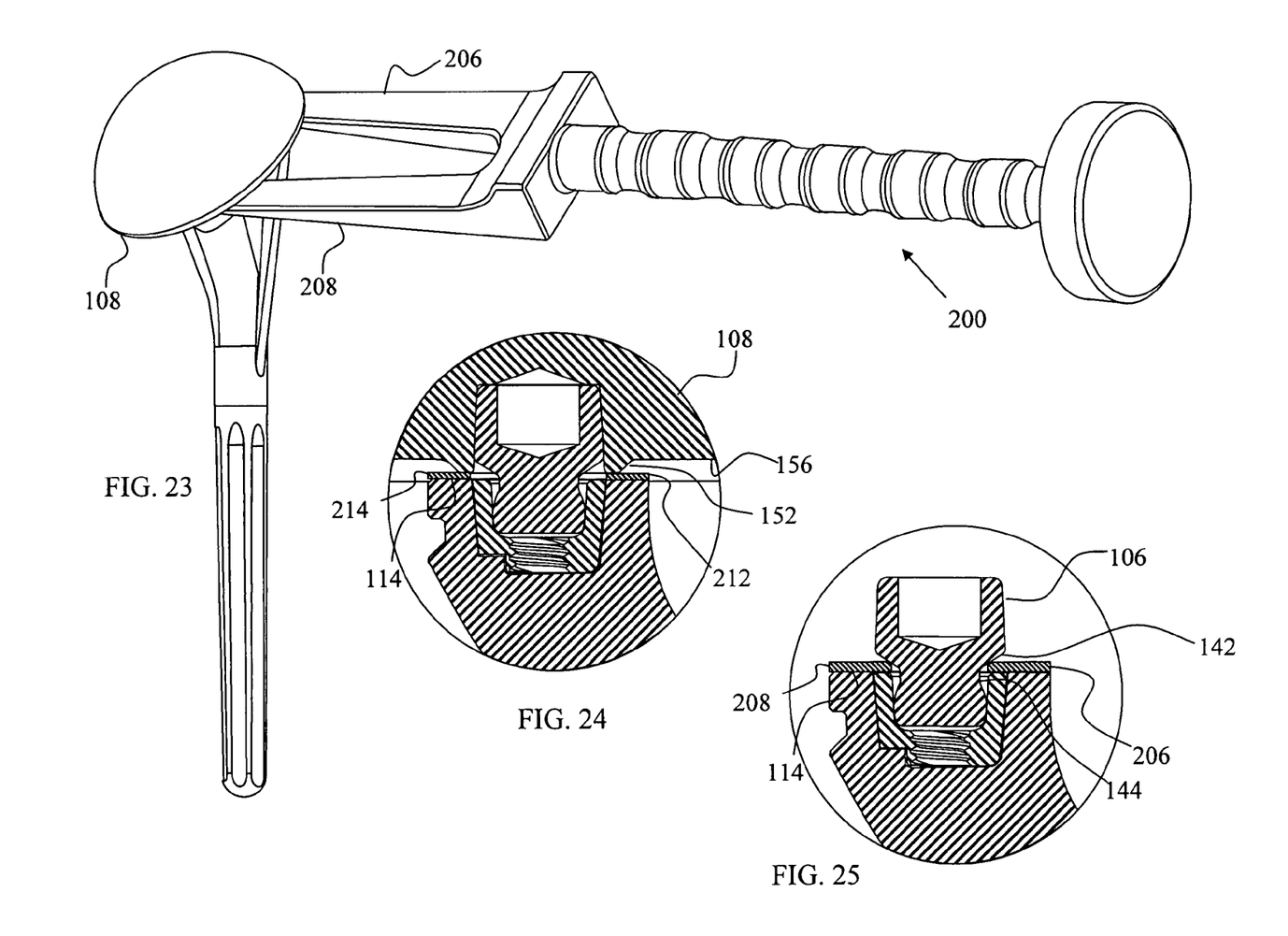
FIG. 23 depicts a perspective view of the removal tool of FIG. 20 positioned to decouple the head of FIG. 1 from the coupler of FIG. 1.
FIG. 24 depicts a partial cross sectional view of the assembled prosthesis assembly of FIG. 1 with the end portions of the prongs of the removal tool of FIG. 20 inserted in the gap between the head and the stem.
FIG. 25 depicts a partial cross sectional view of the assembled coupler and insert of FIG. 1 with portions of the prongs of the removal tool of FIG. 20 inserted between the stem and the shoulder portion of the coupler for decoupling of the coupler and the insert.

Accordingly, disassembly of the assembly 100 is accomplished by maneuvering the prongs 206 and 208 between the articulating head component 108 and the upper surface 114 of the stem 102 as shown in FIG. 23. The recessed area 156 facilitates the positioning of the distal end portions 212 and 214 of the prongs 206 and 208 between the protuberance 152 and the upper surface 114 of the shaft 102 as shown in FIG. 24. Once positioned, the impact knob 210 is impacted. The force of the impact is transferred through the inclined surfaces of the tapered prongs 206 and 208 to the protuberance 152 forcing the articulating head component 108 away from the stem 102. The impact will typically break the coupling between the outer wall 140 of the coupler 106 and the tapered bore 154, allowing the articulating head 108 to be removed from the coupler 106.

The distance between the prongs 206 and 208 decreases from the distance at the distal end portions 212 and 214 and the distance at the base 202. Specifically, the distance between the prongs 206 and 208 at a location between the distal end portions 212 and 214 and the base 202 corresponds to the diameter of the neck 144. Accordingly, once the articulating head component 108 is removed, the prongs 206 and 208 are positioned adjacent to the neck 144 as shown in FIG. 25. The prongs 206 and 208 thus contact the shoulder portion 142 of the coupler 106. If desired, the upper inner surface of the prongs 206 and 208 may be formed with an angle complimentary to the angle of the shoulder portion 142 as shown in FIG. 25. A subsequent impact on the impact knob 210 decouples the coupler 106 from the insert 104.

Figures 26, 27, 28, 29:
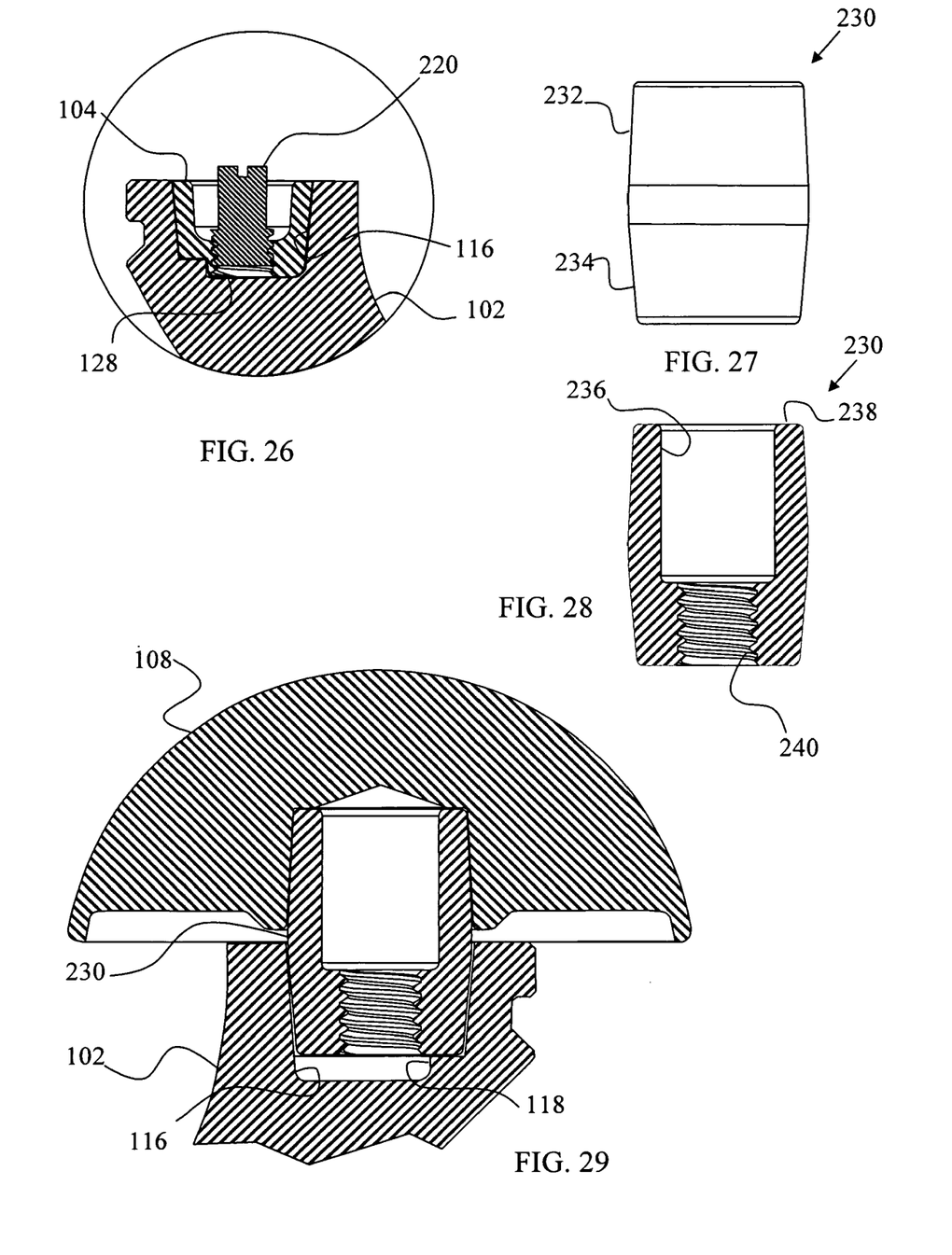
FIG. 26 depicts a partial cross sectional view of the insert and stem of FIG. 1 with a threaded decoupler partially threaded into the threaded bore of the insert for decoupling of the insert and the stem.
FIG. 27 depicts a side plan view of an alternative insert that may be used to couple the head of FIG. 1 with the stem of FIG. 1 with the axis of the head parallel to the axis of the stem receptacle.
FIG. 28 depicts a partial cross sectional view of the alternative coupler of FIG. 27.
FIG. 29 depicts a partial cross sectional view of the stem and head of FIG. 1 assembled using the coupler of FIG. 27.

Finally, the insert 104 is removed by insertion of a threaded decoupler 220 into the threaded bore 128 as shown in FIG. 26. As the threaded decoupler 220 is threaded into threaded bore 128, the threaded decoupler 220 contacts the bottom of the tapered bore 116. Additional rotation of the threaded decoupler 220 breaks the coupling between the insert 104 and the tapered bore 116.

A new humeral prosthetic assembly may then be assembled using the stem 102 along with a new insert 104, a new coupler 106, and a new articulating head component 108. The orientation of the new articulating head component 108 may be set in the manner described above. Instrumentation which may be used to couple the articulating head component 108 and the coupler 106 at the desired orientation with the insert 104 is described in U.S. Publication No. 2005/0288681, published on Dec. 29, 2005, which is herein incorporated by reference.

Subjecting a bone to high impact forces may cause further injury or fracturing of the bone. Additionally, applying high impact forces to an implanted stem could move the stem within the bone resulting in misalignment of the prosthesis. Coupling the insert 104 and the coupler 106 prior to implanting the insert 104 within the bone of a patient thus allows a much higher impact force to be used than would typically be used to form a couple while one of the components is implanted. The use of a higher force provides a stronger coupling which better resists further movement between the components.

Specifically, the impact force used to form the Morse taper coupling between the insert 104 and the stem 102 is passed through the coupler 106. Because the axis of the coupler 106 may not be aligned with the axis 176 of the insert 104, forming the Morse taper coupling applies a torque to the coupler 106 tending to change the alignment of the coupler 106. Since the insert 104 and the coupler 106 may be coupled using a force higher than the force used to form a Morse taper coupling, however, passing the force necessary to couple the insert 104 to the stem 102 through the coupler 106 does not significantly change the alignment of the coupler 106 within the tapered bore 126.

In the event the axis of the tapered bore 154 of the articulating head component 108 is desired to be parallel with the axis of the tapered bore 116, the coupler 106 and insert 104 need not be used. Rather, the insert 230 shown in FIGS. 27 and 28 may be used. The insert 230 includes an upper tapered wall portion 232 and a lower tapered wall portion 234. A bore 236 extends from the upper surface 238 of the insert 230 to a threaded bore 240.

The upper tapered wall portion 232 is configured with a taper that provides a Morse taper coupling with the tapered bore 154 while the lower tapered wall portion 234 is configured with a taper that provides a Morse taper coupling with the tapered bore 116. The insert 230 may thus be used to couple the articulating head component 108 with the stem 102 as shown in FIG. 28 wherein the insert 230 is coupled with the tapered bore 116 at a location above the key member 128.

The humeral prosthesis assembly 100 is thus a modular system that can be used to provide a number of different orientations of an articulating head component with respect to a stem. Accordingly, a kit including stems 102 of different lengths, at least one insert 104, at least one coupler 106, at least one insert 230, and a removal tool 200 provides a highly adaptable system that can accommodate a wide range of joint constructs.

Additional removal systems may be provided in a kit for use with the humeral prosthesis assembly 100. By way of example, a removal tool 250 shown in FIG. 30 may be used to decouple the insert 104 and the insert 230 from the stem 102. The removal tool 250 includes a base 252 and a shaft 254. Two prongs 256 and 258 extend outwardly from the base 252 and an impact knob 260 is located on the shaft 254. The prongs 256 and 258 are similar to the prongs 206 and 208. The prongs 256 and 258, however, are much thicker than the prongs 206 and 208.

Figures 30, 31, 32, 33:
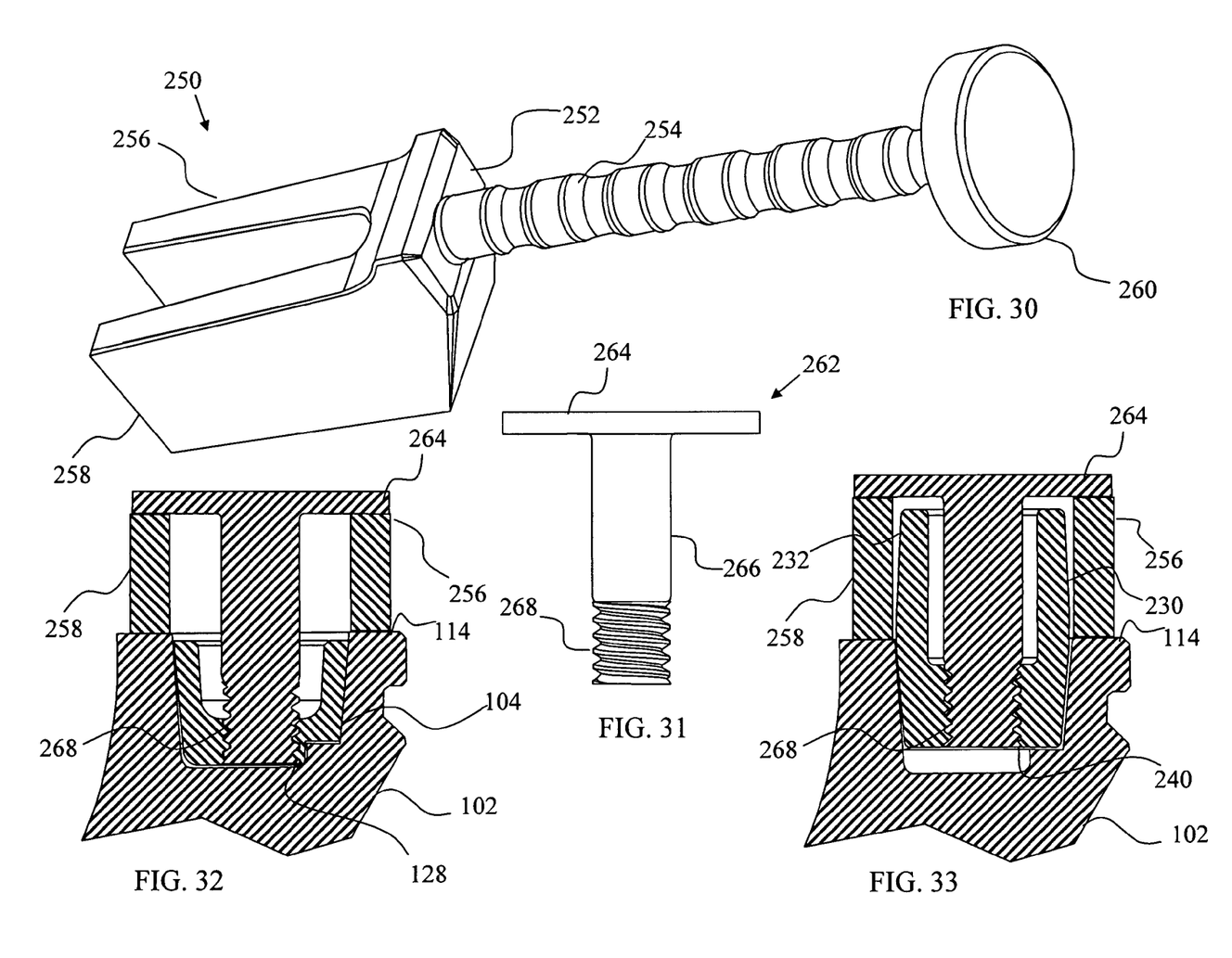
FIG. 30 depicts a perspective view of a removal tool that may be included in a kit and used to decouple the coupler of FIG. 1 from the insert of FIG. 1 or that insert of FIG. 27.
FIG. 31 depicts a side plan view of a decoupler with a threaded stem and a flange that may be included in a kit and used to decouple the coupler of FIG. 1 from the insert of FIG. 1 or the insert of FIG. 27.
FIG. 32 depicts a partial cross sectional view of the insert and stem of FIG. 1 with the decoupler of FIG. 31 threaded into the threaded bore of the insert for decoupling of the insert and the stem.
FIG. 33 depicts a partial cross sectional view of the insert of FIG. 27 and the stem of FIG. 1 with the decoupler of FIG. 31 threaded into the threaded bore of the insert for decoupling of the insert and the stem.

The removal tool 250 is configured to work with a decoupler 262 shown in FIG. 31. The decoupler 262 includes a flange 264 and a stem 266. The stem 266 includes a threaded portion 268. Removal of the insert 104 is accomplished by insertion of the threaded portion 268 of the decoupler 220 into the threaded bore 128 as shown in FIG. 32. The prongs 256 and 258 are then positioned between the flange 264 and the upper surface 114 of the stem 102. Once positioned, the impact knob 260 is impacted. The force of the impact is transferred through the inclined surfaces of the tapered prongs 256 and 258 to the flange 264 forcing the insert 104 away from the stem 102.

Decoupling of the insert 230 is accomplished in a similar manner as the threaded portion 268 of the decoupler 220 is threaded into the threaded bore 240 as shown in FIG. 33. The prongs 256 and 258 are then positioned between the flange 264 and the upper surface 114 of the stem 102. Once positioned, the impact knob 260 is impacted. The force of the impact is transferred through the inclined surfaces of the tapered prongs 256 and 258 to the flange 264 forcing the insert 230 away from the stem 102.

If desired, a different removal tool may be provided for use with each of the inserts 104 and 230. Moreover, other devices may be used to provide an impact to the flange 264.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the embodiments contained herein.

What is claimed is:

1. A prosthesis assembly, comprising:
a stem configured to be implanted in a bone, the stem including a first coupling portion;
a head having a bearing surface configured to mate with at least one of a natural opposing joint component and a prosthetic opposing joint component, the head further having a second coupling portion;
a coupler including a third coupling portion and a fourth coupling portion, the third coupling portion configured to couple with the second coupling portion; and
an insert including (i) a fifth coupling portion configured to couple with the fourth coupling portion so that the insert may assume any one of a plurality of orientations with respect to the coupler, and (ii) a sixth coupling portion configured to couple with the first coupling portion only when the insert assumes a predetermined orientation with respect to the stem,
wherein the first coupling portion comprises a stem receptacle extending inwardly from a proximal end which opens to a surface of the stem, to a closed distal end, the first coupling portion including a first key member and a tapered wall structure between the proximal end and the distal end;
wherein the fourth coupling portion comprises a bulbous portion;
wherein the fifth coupling portion comprises a first insert receptacle extending inwardly from a distal end which opens to a surface of the insert, to a closed proximal end, the first insert receptacle including a tapered wall structure between the proximal end and the distal end;
wherein the sixth coupling portion comprises a tapered wall structure and a second key member configured to mate with the first key member,
wherein (i) the stem receptacle is defined by a receptacle structure, (ii) a distal end portion of the receptacle structure includes a distal interior surface, and (i) the distal interior surface of the receptacle structure defines the first key member, and
wherein (i) a distal end portion of the insert includes a distal exterior surface, and (ii) the distal exterior surface of the insert defines the second key member.

2. The prosthesis assembly of claim 1, wherein:
the second coupling portion comprises a head receptacle extending inwardly from a distal end which opens to a surface of the head, to a closed proximal end, the head receptacle including a tapered wall structure between the proximal end and the distal end; and
the third coupling portion comprises a tapered wall structure.

3. The prosthesis assembly of claim 2, wherein:
the tapered wall structure of the first coupling portion has a taper angle of about 10 degrees;
the tapered wall structure of the second coupling portion has a taper angle of about 5 degrees;
the tapered wall structure of the third coupling portion has a taper angle of about 5 degrees; and
the tapered wall structure of the sixth coupling portion has a taper angle of about 10 degrees.

4. The prosthesis assembly of claim 1, wherein the coupler further comprises:
a neck portion adjacent to the fourth coupling portion; and
a shoulder portion adjacent to the third coupling portion.

5. The prosthesis assembly of claim 4, wherein:
the stem receptacle has a first longitudinal axis;
the coupler has a second longitudinal axis; and
the fifth coupling portion is configured to couple with the fourth coupling portion such that the second longitudinal axis is oriented at any of a plurality of angles with respect to the first longitudinal axis, and
the angle has a magnitude between about 0 degrees and about 30 degrees.

* * * * *